United States Patent [19]

Griffiths et al.

[11] Patent Number: 5,690,955
[45] Date of Patent: Nov. 25, 1997

[54] SUSTAINED RELEASE ALGINATE FIBRE AND PROCESS FOR THE PREPARATION THEREOF

[75] Inventors: Bryan Griffiths, New Tredegar; Pter Michael John Mahoney, Llanarmon, D.C., both of United Kingdom

[73] Assignee: E. R. Squibb & Sons, Inc., Princeton, N.J.

[21] Appl. No.: 338,635

[22] PCT Filed: Jun. 28, 1993

[86] PCT No.: PCT/GB93/01350

§ 371 Date: Nov. 22, 1994

§ 102(e) Date: Nov. 22, 1994

[87] PCT Pub. No.: WO94/00164

PCT Pub. Date: Jan. 6, 1994

[30] Foreign Application Priority Data

Jun. 29, 1992 [GB] United Kingdom ............... 9213773

[51] Int. Cl.⁶ ........................................... A61F 13/00
[52] U.S. Cl. ....................... 424/443; 424/445; 424/448
[58] Field of Search ................................. 424/443, 448, 424/445

[56] References Cited

FOREIGN PATENT DOCUMENTS

| A 0279118 | 8/1988 | European Pat. Off. . |
| A 0439 339 | 7/1991 | European Pat. Off. . |
| A 8901790 | 3/1989 | WIPO . |
| A 9111206 | 8/1991 | WIPO . |
| A 9119470 | 12/1991 | WIPO . |
| A 9222285 | 12/1992 | WIPO . |

Primary Examiner—D. Gabrielle Phelan
Attorney, Agent, or Firm—Theodore R. Furman, Jr.; John M. Kilcoyne

[57] ABSTRACT

An alginate fibre is provided which includes one or more medicaments incorporated into the fibre core such that the one or more medicaments can be released in a sustained manner over time and, optionally, one or more medicaments attached to the surface of the fibre whereby the one or more medicaments attached to the surface of the fibre can be released rapidly therefrom.

19 Claims, 3 Drawing Sheets

SUSTAINED RELEASE ALGINATE FIBRE AND PROCESS FOR THE PREPARATION THEREOF

This application is a 371 of PCT/GB93/01350, filed Jun. 28, 1993.

The present invention relates to a medicament-impregnated alginate fibre. More particularly, the invention concerns a fibre from which medicament can be released in a controlled manner, and to the application of this fibre in the preparation of alginate fabrics and wound dressings.

A number of methods for producing conventional alginate fibres are described in the art. The extrusion of alginate solutions into an aqueous solution containing calcium ions to form yarns of calcium alginate filaments is known, for example, from British Patents Nos. 567641, 568177, 571657 and 624987. Such fabrics were generally prepared by knitting a yarn of calcium alginate filaments and partially converting the calcium alginate to the sodium form to form a calcium/sodium alginate containing, for example, 30–70 percent by weight of the carboxyl groups of the alginate in the calcium form.

U.S. Pat. No. 4,421,583 discloses a process for making a non-woven alginate fabric useful as a wound dressing which comprises spreading a tow of calcium alginate filaments in a flow of water; overfeeding the spread filaments onto a water-previous support so that the filaments cross over each other; and drying the filaments so that the filaments become bonded to each other at their points of contact where they cross over each other. Non-woven alginate fabrics having this high calcium content of 70 to 95 percent are said to be useful for example as throat swabs, which after swabbing are dissolved in sodium hexametaphosphate solution. The non-woven alginate fabrics can be treated such that calcium is partially replaced by sodium, for example by treatment with alcoholic sodium hydroxide and sodium acetate so that from 30 to 70 percent of the carboxyl groups are in the sodium form. The sodium calcium alginate fabrics produced are said to be useful as haemostatic wound dressings which can be absorbed by body fluids, for use for example in deep surgery or after tooth extraction.

WO-A-84/03705 describes a method of producing alginate fibres for fabric of increased solubility in water or saline solutions for application in the medical field and in particular for haemostatic dressings.

U.S. Pat. No. 4,562,110 describes a method of producing dried alginate fibre material which comprises spinning an alginate solution into an aqueous salt bath. The wet-spun continuous fibres of insoluble alginate, in which the fibres are separate but generally parallel, are collected, and the sheet of fibres is laid on a moving conveyor belt which is travelling at a slower speed than the sheet fibre feed speed, so that the fibres become overlaid in a web of defined width. The fibre web is dried and stretched in a manner to reduce the bonding between the fibres. The web is said to be useful as a component of medicated and surgical dressings.

Wound dressings which may incorporate certain medicaments are also known in the art. For example, EP-A-0279118 describes an adhesive product suitable for use on wounds comprising a backing layer of a moisture vapour transmitting continuous polymer film and a layer of a pressure sensitive adhesive containing inter alia at least 30% by weight of alginate. The adhesive product described therein can contain a medicament, such as a chlorhexidine derivative, normally in the adhesive layer. Alternatively, the medicament may form part of the alginate polymer used for the pressure sensitive adhesive layer, suitable examples being stated to include silver, copper and zinc derivatives of sodium alginate.

Additionally, U.S. Pat. No. 4,753,231 discloses the incorporation of such antibacterial agents as silver sulphadiazine, povidone-iodine, chlorhexidine salts such as gluconate, acetate and hydrochloride, and quaternary agents such as benzalkonium chloride into a wound dressing pad.

Moreover, U.S. Pat. No. 4,817,594 discloses wound dressings as supports for therapeutic or antiseptic materials including iodine, formol, lime, oxygen, bacillary toxins and the like.

The commercially available products Bactigras and Serotulle, obtainable respectively from Smith and Nephew Ltd., Hull, United Kingdom, and Seton Healthcare Group, Oldham, United Kingdom, both consist of paraffin gauze impregnated with the antibacterial agent chlorhexidine.

The medicated wound dressings of the prior art comprise medicaments absorbed onto the surface of the fibres making up the wound dressing. Such surface-bound medicaments are expected to be released rapidly in the environment of use. For a variety of clinical applications, it is considered desirable to provide a controlled release of the same or a different medicament to a wound over time. If the medicament were merely applied topically throughout the treatment regimen, this would require frequent removal and replacement of the dressing, with concomitant inconvenience and risk of opportunistic infection.

We have now found that a medicament-containing alginate fibre can be prepared which allows for the sustained release of the medicament over time.

The present invention accordingly provides an alginate fibre comprising one or more medicaments incorporated into the fibre core such that the or each medicament can be released in a sustained manner over time.

As used herein, "incorporated into the fibre core" means encased within the fibre and is to be contrasted with the situation where medicament is attached to the surface of the fibre.

The time taken for substantially all of the medicament or medicaments incorporated into the fibre core to be released will depend on such factors as the nature of the medicament (s) used, the amount of medicament(s) used, and the permeability of the alginate fibre. Different release periods will be required for different clinical situations. Typically the or each medicament will be released into the environment of use over a period of hours, days or weeks. For example, where the fibres of the invention are being used in a wound dressing, the time taken for complete release of medicament incorporated into the core of an alginate fibre might be in the range of 1–7 days, for example 4–5 days.

It may frequently be desirable in the treatment or management of wounds to provide for the possibility of administering a medicament to a wound in a rapid initial burst, followed by a slower controlled release of the same or a different medicament to the wound. By way of example, an antibacterial or antiseptic agent such as chlorhexidine is generally applied promptly to a wound in appreciable quantities so as to achieve a rapid initial kill of deleterious micro-organisms, but this is desirably followed up with further quantities of the medicament in smaller amounts over a sustained period in order to prevent or inhibit bacterial regrowth.

Accordingly, in a further aspect, the present invention provides an alginate fibre comprising one or more medicaments incorporated into the fibre core and one or more medicaments attached to the surface of the fibre, whereby the or each medicament attached to the surface of the fibre can be released rapidly therefrom, whilst the or each medicament incorporated into the fibre core is released in a sustained manner over time.

The rate of release of a medicament attached to the surface of the fibre will be determined by a number of factors such as the nature of the medicament and the nature of the environment of use. Typically substantially all of the medicaments attached to the fibre surface will be released over a period of minutes or hours, usually in the region of 5–60 minutes.

Incorporation of one or more medicaments into an alginate fibre can be accomplished by a modification of well-known procedures for the preparation of alginate fibres. Procedures for the preparation of alginate fibres are described in, for example, British Patents Nos. 567641, 568177, 571657 and 624987. Essentially these procedures comprise extruding an aqueous solution of a water soluble alginate into a bath containing a salt of a metal which forms a water insoluble alginate, such as, for example, calcium chloride, so as to form a thread.

We have now found that, if one or more medicaments is (are) included in the solution of water soluble alginate, when the solution, known as the "dope", is extruded or spun into a solution of ions which form an insoluble alginate, a fibre is formed having the medicament(s) encased in the fibre core.

The present invention accordingly provides a process for the preparation of an alginate fibre comprising one or more medicaments incorporated into the fibre core, which process comprises spinning a solution of an alginate together with one or more medicaments.

One or more medicaments may be attached to the surface of the fibres according to the invention by physical or chemical means. Typical examples of attachment by physical means include hydrogen bonding, adsorption and van der Waals interaction. Alternatively, some kind of chemical interaction between alginate molecule and medicament molecule may occur, resulting in cross-linking between the alginate and medicament moieties. A typical example of attachment by chemical means is ionic interaction, such as salt formation. For example, chlorhexidine gluconate, which is the gluconate salt of a cationic bisbiguanide derivative, possesses an appreciable potential positive charge and has been found to interact significantly with the negatively-charged alginate molecule.

As will be appreciated, where the alginate fibre according to the present invention comprises one or more medicaments incorporated into the fibre core and one or more medicaments attached to the surface of the fibre, the individual medicaments incorporated into the fibre core and attached to the surface of the fibre may be the same or different. Preferably, a single medicament will be incorporated into the fibre core; and likewise a single medicament will preferably be attached to the surface of the fibre. In a particularly preferred embodiment, a single medicament is both incorporated into the fibre core and attached to the surface of the fibre, the medicament at each location being identical.

There is in principle no restriction on the types of medicament which can be employed in conjunction with the alginate fibre according to the invention. It will nevertheless be understood that the or each medicament to be incorporated into the fibre core must be compatible in the sense that it should not interfere with the spinning process by which the basic alginate fibre is produced. Similarly, it will be understood that the or each medicament to be attached to the surface of the fibre will be such as to be capable of attachment thereto by one or other of the means of attachment indicated above. Suitable medicaments for use in conjunction with the alginate fibre according to the invention include antibacterial agents, for example bisbiguanide derivatives such as chlorhexidine, both in the free base form and as the acetate, gluconate or hydrochloride salts, tetracycline derivatives such as chlorotetracycline; oxytetracycline and tetracycline itself, and sulphonamide derivatives such as sulphadiazine; antiprotozoal agents, for example imidazole derivatives such as metronidazole; antifungal agents such as chlorphenesin; phenothiazine derivatives such as promethazine and chlorpromazine; nucleosides such as iodouridine; hormones such as noradrenalin; and anti-inflammatory agents, for example steroid derivatives such as hydrocortisone and prednisolone. Preferred medicaments for use in conjunction with the alginate fibre according to the invention include chlorohexidine, chlortetracycline, promethazine, noradrenalin and prednisolone. Particularly preferred are chlorohexidine and chlorotetracycline, especially chlorhexidine, in both the free base and salt forms, more especially chlorhexidine acetate.

Depending upon the type(s) of medicament incorporated into the core and, optionally, attached to the surface, the fibre according to the invention may possess a variety of advantages. In particular, as indicated previously, an antibacterial or antiseptic agent such as chlorhexidine may advantageously be both incorporated into the fibre core and attached to the surface of the fibre; a burst of medicament from the surface of the fibre will achieve a rapid initial kill of bacteria, whilst a sustained "follow-up" of smaller quantities of medicament from the fibre core will deal with bacterial regrowth. For more complex medical conditions different medicaments may advantageously be incorporated into the fibre core and attached to the surface of the fibre. For example, the medicament incorporated into the fibre core may be an antifungal agent whereas the medicament attached to the surface of the fibre may be an antibacterial agent; or vice versa, as necessary. Alternatively a binary system might be envisaged, whereby the component released from the surface of the fibre is initially in the form of an inactive prodrug and only becomes activated, i.e. converted into the active medicament, upon subsequent release of the core component, with which the prodrug interacts. Byway of illustration, the medicament incorporated into the fibre core might be an antibacterial sulphonamide derivative such as sulphadiazine, whilst the agent attached to the surface of the fibre might comprise silver ions, which themselves are known to possess appreciable antibacterial activity; rapid release of the silver ions into the medium would be followed by a slower release from the core of sulphadiazine, which would interact with the silver ions and give rise to a product exerting a synergistically enhanced antibacterial effect relative to that exerted by either component alone.

The amount of medicament incorporated into the fibre core will in general depend upon such factors as the solubility and stability of a given medicament in the alginate dope from which the basic fibre is to be spun. It may also depend upon the reactivity of a given medicament with the alginate dope, since this may result in an unspinnable mixture. For example, chlorhexidine hydrochloride has been found to be relatively insoluble in the alginate dope, resulting in a core concentration of medicament of 0.2% w/w at most. Similarly, non-polar species such as steroids are also relatively insoluble in the alginate dope and thereby give rise to fibres possessing a core concentration of medicament of approximately 0.1% w/w. Moreover, chlorhexidine gluconate, which, as mentioned above, has been found to cross-link extensively with the alginate molecule, gives rise to unspinnable mixtures at medicament concentrations of well below 1.0% w/w. On the other hand, chlorhexidine acetate has been found to perform well in the presence of the alginate dope, with the result that core concentrations of medicament in the region of 1.0% w/w are readily achievable. As a general rule, the concentration of medicament within the fibre core is suitably from 0.01% to 2.0% w/w, preferably from 0.5% to 1.5% w/w.

The amount of medicament attached to the surface of the fibre will also be dependent upon various factors. These include, for example, the ability of a given medicament to become adsorbed to the surface of the pre-formed alginate fibre, or to cross-link chemically with the alginate structure. In general, the concentration of medicament attached to the surface of the fibre according to the fibre according to the invention is suitably from 0.01% to 2.0% w/w, preferably from 0.5% to 1.5% w/w.

In a further aspect, the present invention provides a process for preparing an alginate fibre comprising one or more medicaments incorporated into the fibre core and one or more medicaments attached to the surface of the fibre, which process comprises the following steps:

(1) spinning a solution of an alginate together with one or more medicaments in order to produce a fibre incorporating the or each medicament within its core; and (2) modifying the resulting fibre by attachment of one or more medicaments to the surface thereof.

Suitable alginates for use in the processes according to the invention include both water-soluble and water-insoluble alginates, but will most preferably be water-soluble alginates. A particular water-soluble alginate for use in the spinning procedure is sodium alginate. Nevertheless, the sodium alginate may advantageously contain up to 1.5% by weight of calcium ions. Examples of specific sodium alginate products of use in the process according to the invention include Manucol DM, which is available from Kelco International Limited, and Protan LF 10/60, which is available from Protan Limited.

Depending upon the nature of the alginate and/or medicament(s) employed, the spinning procedure may be tailored as required. For example, if a highly water-soluble medicament is employed, so-called solvent suppression may be required to prevent the medicament being leached from the fibre during subsequent processing; this involves the addition of a water-miscible organic solvent, such as acetone or isopropanol, to the medicament-containing alginate dope.

Attachment of one or more medicaments to the surface of the pre-formed alginate fibre may conveniently be accomplished by one or other of a variety of standard procedures. Which method is adopted will, for example, be dependent upon the relative ability of a given medicament to become adsorbed to the pre-formed alginate fibre, or upon its capacity for chemically cross-linking with the alginate structure. Again, the procedure can be tailored as required depending upon the nature of the alginate and/or medicament(s) employed.

For instance, the medicament-containing alginate fibre obtained from step (1) of the above decribed process may be immersed in a bath containing an aqueous solution of a given medicament or medicaments; this procedure will clearly be particularly amenable to appreciably water-soluble medicaments such as chlorhexidine. If necessary, a water-miscible cosolvent such as acetone may be employed in the bath. The fibre may advantageously be dragged through the bath in order to promote the required amount of adsorption and/or cross-linking at an acceptable rate. The duration of immersion of the fibre in the medicament solution may dictate the amount of medicament which is ultimately adsorbed and/or cross-linked; this suggests that a measure of quality control can be exercised over the production of the final fibre, permitting a range of fibres to be prepared having a variety of concentrations of medicament attached to the surface, and hence a corresponding range of amounts of medicament capable of being released rapidly therefrom.

Alternatively, a solution of the or each medicament in a volatile solvent such as acetone may be sprayed onto the pre-formed alginate fibre obtained from step (1) of the above-described process; upon evaporation of the volatile solvent, a finished fibre results to which a certain amount of medicament adheres, for example by adsorption and/or chemical cross-linking. As will be appreciated, this procedure lends itself particularly appealingly to relatively poorly water-soluble medicaments such as metronidazole.

The permeability of the finished fibre will be influenced by the molecular structure of the particular alginate employed. Alginates are block copolymers consisting of guluronate and mannuronate, i.e. sugar-derived, residues. One factor influential in determining permeability will be the particular block structure of the actual polymer employed, i.e. the precise distribution within the molecule of the blocks of guluronate and mannuronate residues. A high proportion of guluronate blocks is known to promote a good propensity for chelation of calcium ions. This in turn means that a high ratio of guluronate to mannuronate blocks can lead to a fibre having a lower permeability, whereas a low ratio of guluronate to mannuronate blocks will afford a more permeable fibre.

Alginates which comprise a high proportion of guluronate residues are known as high G alginates, and alginates which comprise a low proportion of guluronate residues are known as low G alginates. Both high G alginates and low G alginates are suitable for use in the present invention.

Control of the amount of medicament incorporated into the fibre core, and hence of the rate of release of medicament from the fibre core, is achievable by varying the concentration of the solution in the bath from which the fibre is spun.

Another factor influencing the amount of medicament incorporated into the fibre core is the solubility of the medicament in the spin bath. Certain medicaments are highly pH-dependent, and it is therefore advisable to maintain the solution within the spin bath at a constant optimum pH. For example, in the case of chlorhexidine the spin bath solution is ideally kept at a pH below 6.0.

Conventional fibre spinning processes usually involve a drying stage, towards or at the end of the procedure. Drying may suitably be effected in an acetone bath, or by means of heat. In the latter case, a less dense fibre results than if acetone drying is involved; this difference may again afford a valuable means of controlling the permeability of the fibre core, and hence the rate of release of medicament therefrom. Losses of medicament from the fibre core during the acetone drying stage may be encountered. This effect may be controlled by varying the pH of the acetone drying bath(s) as required.

In another aspect, the present invention provides an alginate fabric formed in whole or in part from the alginate fibre according to the invention.

The alginate fabric in accordance with the invention may, for example, be non-woven, woven or knitted. Preferably, the fabric is non-woven, not only from the standpoint of ease of manufacture but also because of the general dimensional stability of non-woven fabrics, which are acknowledged not to stretch so easily as, for example, knitted fabrics.

In the preparation of a non-woven fabric, a cotton card may be used to form a web, which may then be cross-lapped, for example with a Garnet Bywater cross-lapper, and then needle punched in a Garnet Bywater needle loom. In the preparation of a woven fabric, the precursor alginate fibres may be carded and then spun into a yarn, which can be woven in a conventional loom. Alternatively, the fibres may be collected in a spinning box, according to the method described in British Patent No. 568177, and woven. In the preparation of a knitted fabric, the fibres can be prepared as a continuous filament yarn, again according to the method described in British Patent No. 568177, which is then knitted on a conventional knitting machine.

The present invention further provides a wound dressing comprising an alginate fabric according to the invention.

As used herein, the expression "wound dressing" includes surgical dressings. The term "wound" includes burn, scald, cut, sore, ulcer, blister, rash or any other lesion or area of troubled skin.

When adapted for use in the treatment of burns or scalds, the wound dressing of the invention may advantageously contain, either incorporated into the core of the fibres constituting the dressing or attached to the surface thereof, or both, one or more antimicrobial agents known to be of particular efficacy in preventing or inhibiting infection at the burn or scald site. Such antimicrobial agents suitably include metronidazole, and sulphonamide derivatives.

In order to prevent or retard the biological degradation of the alginate fibre constituents, the wound dressing of the invention will advantageously incorporate conventional preservatives, for example Metasol D3T (Merck), Parasept (methyl paraben) (Kaloma Chemical) or Bromopol (2-bromo-2-nitro-1,3-propanediol) (Boots Ltd.).

The wound dressings encompassed by the invention may comprise one or more of the wound dressing components well known in the art. For example, the wound dressing may comprise one or more adhesive layers. The adhesive layers may independently comprise a continuous or non-continuous layer, typically of thermoplastic. Each of these layers may be impervious to moisture or vapour. In the alternative the layer may be semipermeable. Suitable materials have a softening point of 70° to 120° C. and may be polyamides such as polycaprolactam and other "nylons", and also polycarbonates or polyurethanes. Such materials may have a pore size of less than 20 μm. They may be water vapour transmissive (200 to 2000 g/m$^2$/24 hr) at the standard relative humidity of 100% and standard temperature of 37° C. The effective pore size may be less than 2 μm.

The wound dressing may also comprise one or more absorbent layers. The absorbent layers may independently include, in addition to the alginate fibres of the invention, karaya gum, locust bean gum, guar gum, sodium acrylate, polyvinyl alcohol, pectin, gelatin, carboxymethylcellulose, high molecular weight carbowaxes, carboxy polymethyl collagen, cotton and carbon.

The wound dressing may also comprise a separate and discrete layer which faces the wound. This wound facing layer may optionally be a non-adhering semipermeable thermoplastic selected from the class described above.

The size and shape of the wound dressing may be defined as desired. Typically the wound dressing will be approximately circular or rectangular and may have length or width or diameter of from 1 to 200 cm.

The wound dressings formed from the alginate fabric according to the present invention will advantageously be conventional dressings well known in the art. Examples of suitable dressings include bandages, adhesive strip dressings, island dressings, pads of various kinds, surgical sponges and packs, ward dressings of the type sold under the registered Trade Mark "Steripad", and such articles as tampons which may, for example, be impregnated with an antifungal agent such as miconazole for the treatment of candidal vaginitis (vaginal thrush). Such dressings may conveniently be prepared by standard methods known from the art.

The dressings in accordance with the present invention will conveniently be packaged in a hermetically-sealed envelope and sterilised, e.g. with ethylene oxide or by gamma-irradiation.

In a still further aspect, the present invention provides a method of treating a wound which comprises the application to a wound of a wound dressing according to the invention.

BRIEF DESCRIPTION OF THE DRAWINGS

Embodiments of the invention will now be described by way of example and with reference to the accompanying drawings, in which.

METHOD A

Basic Method for Preparation of Alginate Fibres containing Chlorhexidine

Figure 1:
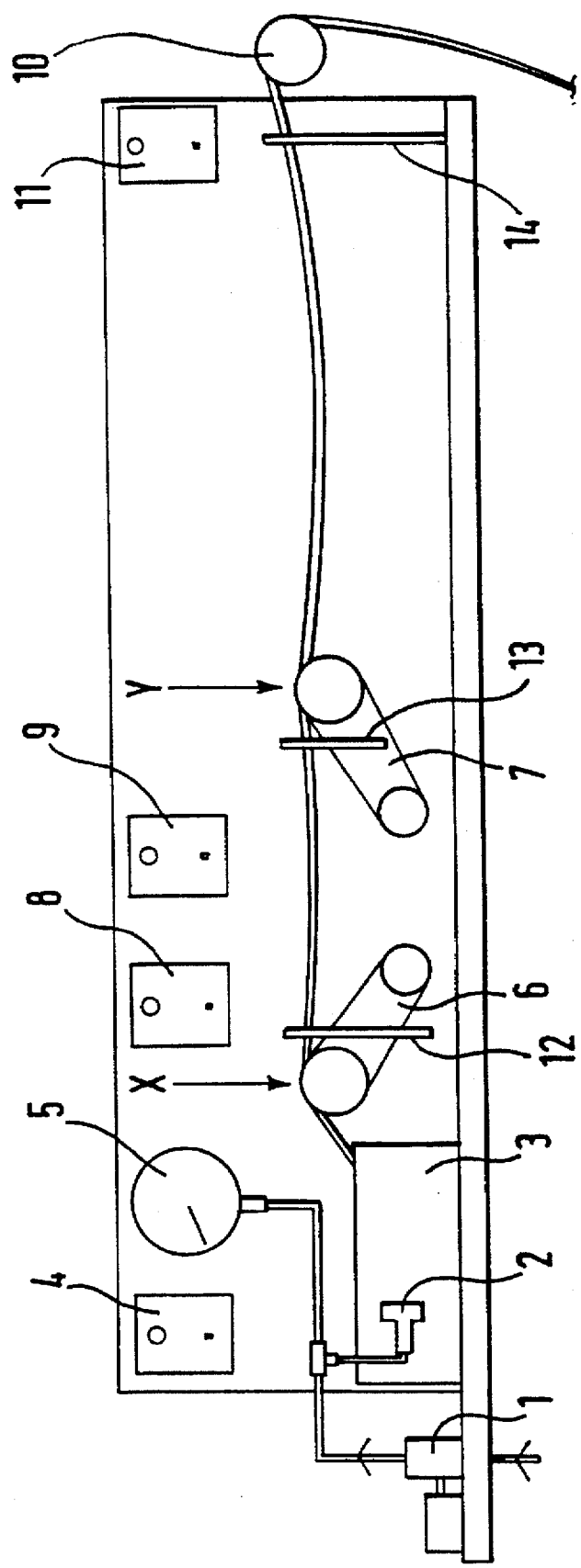
FIG. 1 is a schematic representation of a suitable apparatus for preparing alginate fibre comprising medicament incorporated into the fibre core.

Alginate dope containing chlorhexidine was prepared by dissolving sodium alginate (5 g) in deionised water (95 ml) containing the appropriate amount of chlorhexidine diacetate (0.05 g). The mixture was stirred using a Silverson mixer until obvious particulate matter had been dispersed. The mixture was then allowed to stand for 24 hours. Using the apparatus depicted schematically in FIG. 1, the mixture was extruded, by means of pump 1, through a 400 hole spinneret 2 into a bath 3 containing a solution of calcium chloride and sodium chloride. The rate of extrusion could be controlled by means of the pump speed controller 4 in conjunction with pressure gauge 5. The resulting fibre was stretched between two godets 6 and 7, whose operation was controlled by godet controllers 8 and 9 respectively. The fibre was then collected on a wind-up spool 10, itself controlled by controller 11. The direction of passage of the nascent fibre through the apparatus was controlled by fibre guides 12, 13 and 14. The collected fibre was then dried using acetone, and the acetone driven off in a stream of warm air. Yield, 4.5 g fibre; chlorhexidine diacetate content 0.5% w/w.

METHOD B

Analytical Method for Determination of Chlorhexidine Diacetate Content in Fibres 3.0 mg of chlorhexidine diacetate was dissolved in 20 ml of 2N hydrochloric acid and then treated as described below. By a process of dilution, solutions containing 2.4 mg, 1.8 mg, 1.2 mg and 0.6 mg of chlorhexidine diacetate were prepared and treated in similar fashion. Absorptions were determined at 475 nm and a calibration curve prepared.

400 mg of the fibre, prepared as described in Method A above, was weighed out, and placed in a small beaker. The fibre was cut into small pieces to ensure complete extraction of the chlorhexidine. 20 ml of 2N hydrochloric acid was added, and the mixture agitated. This was then filtered under vacuum. The filtrate was placed in a 100 ml volumetric flask. The volume was adjusted to about 80 ml with deionised water. 5.0 ml of cetrimide solution (prepared by dissolving 20 g of cetrimide B.P. in 80 ml of warm deionised water; cooling; and diluting to 100 ml) was added, then 2.0 ml of alkaline sodium hypobromite, prepared as described below. If necessary, small amounts of sodium hydroxide were added until the solution was alkaline; this point was detected by a colour change in the solution from yellow to orange. The solution was then made up to 100 ml using deionised water. Absorption was then determined at 475 nanometers, and the chlorhexidine diacetate content of the fibre could thence be calculated with reference to the calibration curve obtained as described above.

The alkaline sodium hypobromite reagent utilised in the above-described procedure can be prepared as follows:

Place 5 ml of bromine in a measuring cylinder. Add to 400 ml of sodium hydroxide solution, which has been prepared by adding 10 g of sodium hydroxide to 400 ml of deionised water in a concial flask. Stir until all the bromine has gone into solution. Adjust the volume of this solution to 500 ml with deionised water. The working reagent is prepared by diluting 100 ml of the resulting solution to 150 ml with deionised water. Place 132 ml in a measuring cylinder, and add 66 ml of 3N sodium hydroxide. This is stable for about one month.

METHOD C

Release of Chlorhexidine from Fibres

Fibre, prepared as described in Method A above, was cut up into twenty-four 100 mg samples as follows:

A length of fibre was cut from the main body of the fibre, i.e. from one particular area. This was then cut up into three 100 mg samples of equal lengths (labelled a, b and c respectively), keeping a further 100 mg off-cut to be used as the control sample for each batch (labelled Control). Each 100 mg sample was then placed in small, individual sample vials, labelled accordingly. Samples a, b and c had 2 ml of a pure culture of *Pseudomonas aeruginosa* added to them, ensuring all the fibre was covered. The Control sample for each batch was left unaltered. All samples were incubated at 37° C. for 75 min, and the above procedure was repeated for corresponding samples for other specific periods of time— 150 min, 225 min, 300 min, 375 min and 450 min— requiring twenty-four samples in all.

The samples were then analysed for chlorhexidine content as described in Method B above. A mean value of the individual a, b and c readings for each incubation period was calculated, and the results obtained are displayed in Table 1 below and also depicted in FIG. 2, which plots the percentage of chlorhexidine released against time (as used herein, CX is an abbreviation for chlorhexidine).

TABLE 1

| Incubation Time (minutes) | Amount of CX Released (%) |
|---|---|
| 75 | 20 |
| 150 | 27 |
| 225 | 24 |

TABLE 1-continued

| Incubation Time (minutes) | Amount of CX Released (%) |
|---|---|
| 300 | 31 |
| 375 | 30 |
| 450 | 38 |

Figure 2:
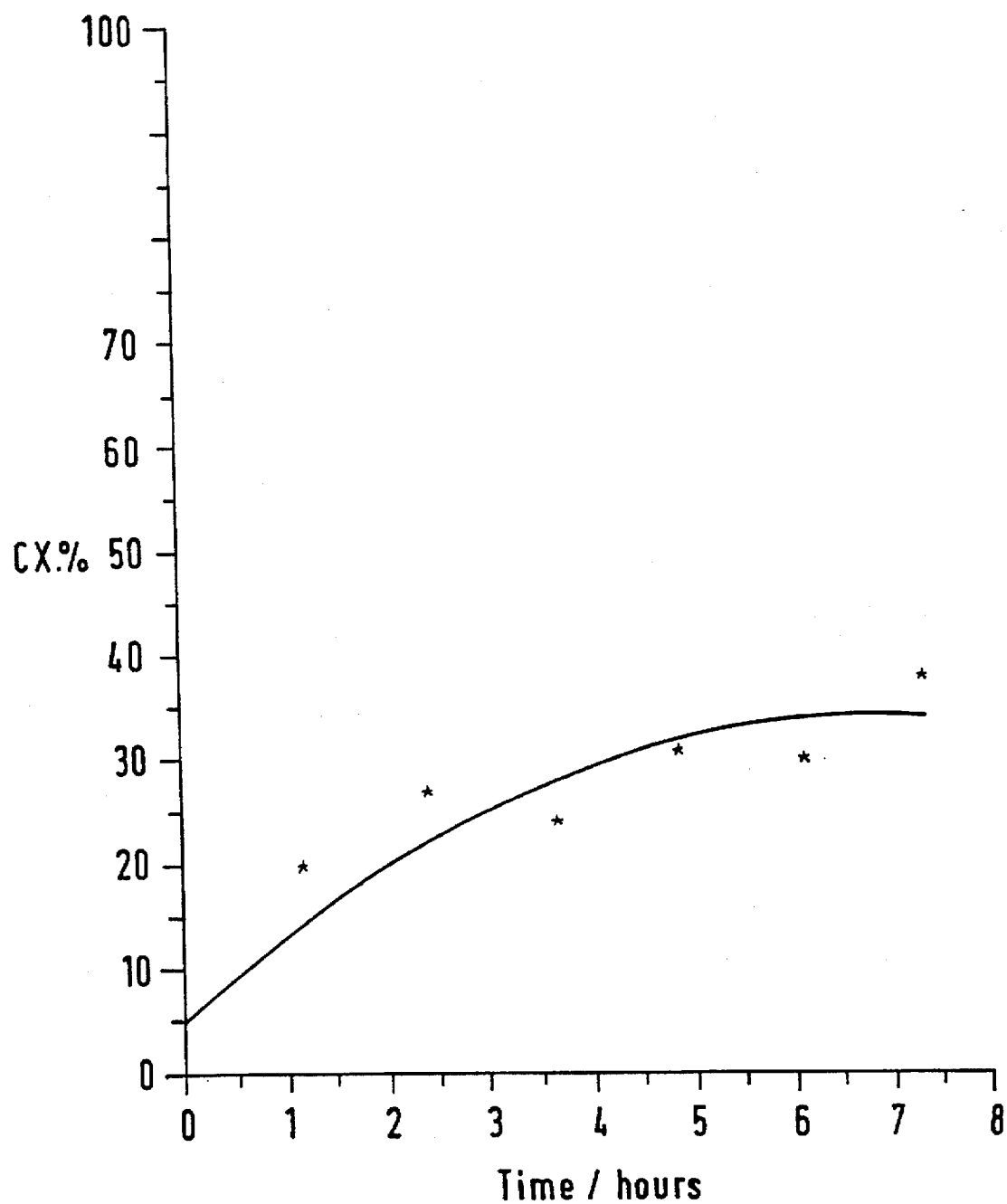
FIG. 2 is a plot of percentage release of chlorhexidine as a function of incubation time for an alginate fibre comprising chlorhexidine incorporated into the fibre core.

From Table 1 and FIG. 2, it can be seen that a steady sustained release of chlorhexidine from the fibre core occurs with time.

METHOD D

Preparation of Alginate Fibre with Chlorhexidine Diacetate on the Fibre Surface 3 l of a saturated solution of chlorhexidine diacetate in deionised water was prepared. Approximately 8 cm lengths of calcium alginate fibre tow were immersed in this solution for known lengths of time. The samples were then dried by brief immersion in acetone, the acetone subsequently being driven off in a stream of warm air. The fibre samples were then analysed as described in Method B above. The results obtained are displayed in Table 3 below and also depicted in FIG. 3, which plots the concentration of chlorhexidine diacetate attached to the fibre surface as a function of the immersion time.

TABLE 3

| Immersion time (sec) | Concentration of Chlorhexidine diacetate on fibre surface (mg/g fibre) |
|---|---|
| 5 | 0.9575 |
| 10 | 1.0925 |
| 15 | 1.4475 |
| 30 | 1.8300 |
| 60 | 1.8725 |
| 120 | 8.8300 |
| 180 | 8.7525 |
| 300 | 13.6525 |

Figure 3:
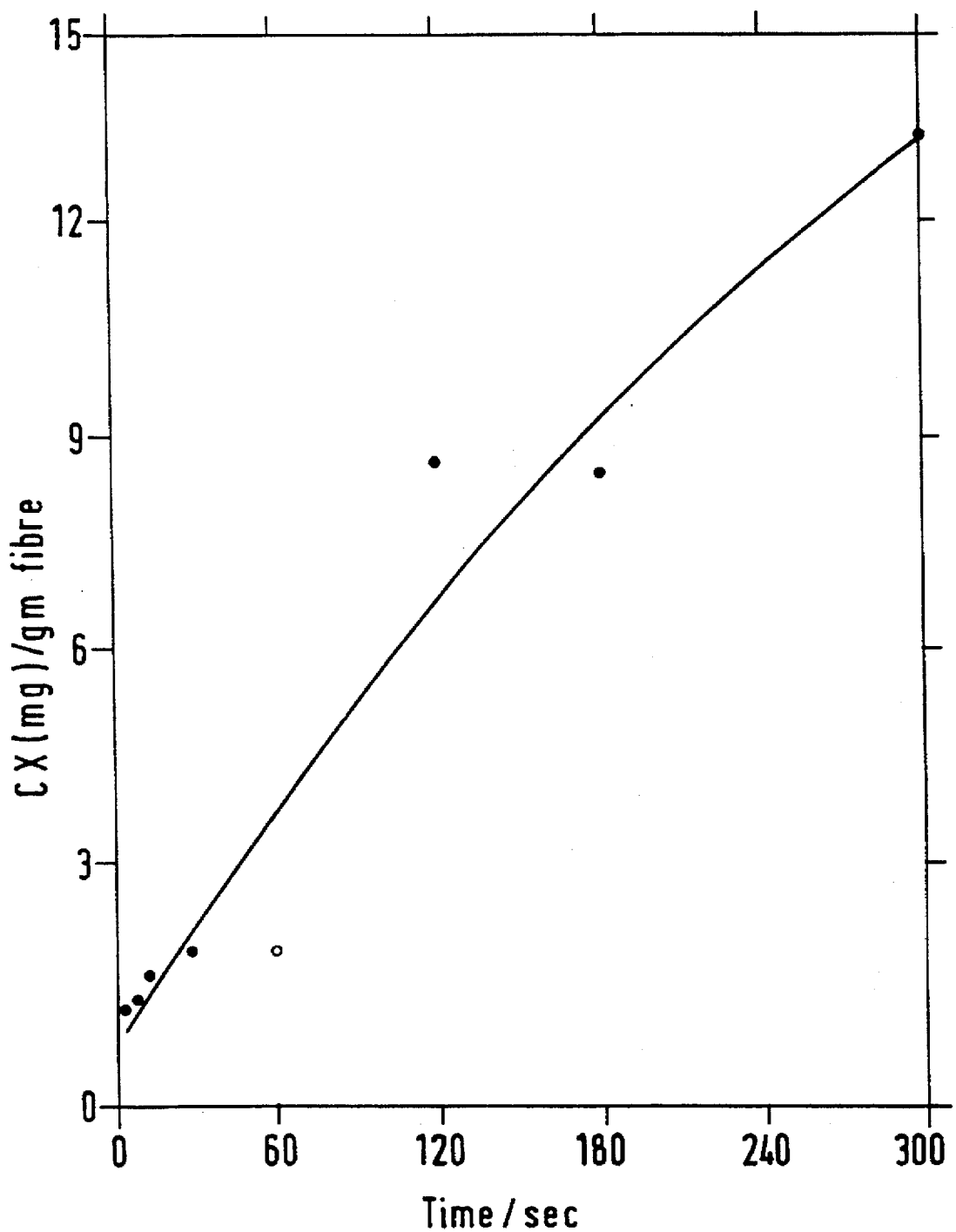
FIG. 3 is a plot of the concentration of chlorhexidine in mg per gram of fibre attached to the surface of alginate fibre as a function of the duration of immersion of the unloaded fibre in a chlorhexidine bath.

As will be seen from FIG. 3, the concentration of chlorhexidine which becomes attached to the fibre surface is essentially proportional to the duration of immersion of the fibre in the chlorhexidine diacetate solution bath.

METHOD E

Experiment to Determine Viability of Chlorhexidine after Attachment to Surface of Alginate Fibre A non-irradiated sample of fibre which had been treated with chlorhexidine on its surface, as described in Method E above, was used to determine the range of bacterial susceptibility. The following bacterial strains were selected for testing:

| | |
|---|---|
| *Candida albicans* | NCPF 3255 |
| *Pseudomonas aeruginosa* | NCTC 10322 |
| *Escherischia coli* | NCTC 9001 |
| *Proteus vulgaris* | NCTC 4175 |

Four 10 ml samples of tryptone soya broth were inoculated with each strain and a plate count done on each. Then a 100 mg sample of the fibre was added to half the broths and the remainder left as controls. Those broths to which fibre had been added were then sampled again and then at hourly intervals, by removing 0.1 ml aliquots plated out onto nutrient agar, the control broths being sampled only at the beginning and the end of the experiment. The results obtained are displayed in Table 4 below.

TABLE 4

| Time (mins) | Ps | Ps(D) | Pr | Pr(D) | Can | Can(D) | Esc | Esc(D) |
|---|---|---|---|---|---|---|---|---|
| A. 100 mg of fibre in 10 ml of inoculated broth ||||||||| 
| 0 | U/C | U/C | 38 | 32 | U/C | U/C | U/C | U/C |
| 5 | U/C | U/C | 70 | 60 | U/C | U/C | U/C | U/C |
| 60 | 50 | 24 | 0 | 0 | 6 | 1 | 0 | 0 |
| 120 | 21 | 50 | 0 | 0 | 1 | 0 | 0 | 0 |
| 180 | 6 | 1 | 0 | 0 | 0 | 0 | 0 | 0 |
| 240 | 0 | 0 | 0 | 0 | 0 | 0 | 0 | 0 |
| 300 | 0 | 8 | 0 | 0 | 0 | 0 | 0 | 0 |
| 360 | 0 | 4 | 0 | 0 | 0 | 0 | 0 | 0 |
| B. Control broth samples ||||||||| 
| 0 | U/C | U/C | 52 | 46 | U/C | U/C | U/C | U/C |
| 360 | C | C | U/C | U/C | U/C | C | C | C |

U/C = an uncountable number of colonies
C = confluent growth
Can = *Candida albicans* NCPF 3255
Ps = *Pseudomonas aeruginosa* NCTC 10322
Esc = *Escherischia coli* NCTC 9001
Pr = *Proteus vulgaris* NCTC 4175
(D) = duplicate measurement From the results displayed in Table 4 above it is apparent that chlorhexidine is not inactivated by attachment to alginate fibres, since all bacterial strains tested showed a high degree of sensitivity to chlorhexidine released from the fibre surface. This compound was demonstrably active within the first hour of incubation, and remained active throughout the six hours of testing. These results apparently contradict various reports in the literature, which suggest that chlorhexidine becomes deactivated upon contact with alginate.

We claim:

1. An alginate fibre comprising one or more medicaments incorporated into the fibre core, and one or more medicaments attached to the surface of the fibre, wherein the concentration of medicament attached to the surface of the fibre is 0.01% to 2.0% w/w, whereby the one or more medicaments attached to the surface of the fibre can be released therefrom over a period of minutes or hours, and the one or more medicaments incorporated into the fibre core can be released in a sustained manner over a period of hours, days or weeks.

2. An alginate fibre as claimed in claim 1, wherein the concentration of the medicament attached to the surface of the fibre is 0.5 to 1.5% w/w.

3. An alginate fibre as claimed in claim 1 or 2, wherein the one or more medicaments is selected from antibacterial agents, antiprotozoal agents, antifungal agents, promethazine, chlorpromazine, nucleosides, hormones and anti-inflammatory agents.

4. An alginate fibre as claimed in claim 3 wherein the one or more medicaments is selected from chlorhexidine, chlortetracycline, promethazine, noradrenalin and prednislolone.

5. An alginate fibre as claimed in any one of claims 1, 2 or 4 wherein a single medicament is incorporated into the fibre core.

6. An alginate fibre as claimed in claim 5 wherein a single medicament is attached to the surface of the fibre.

7. An alginate fibre as claimed in claim 6 wherein the medicament is chlorhexidine or a salt thereof.

8. An alginate fibre as claimed in claim 7 wherein the medicament is chlorhexidine acetate.

9. An alginate fibre as claimed in claim 1 wherein a single medicament is incorporated into the fibre core and a single medicament is attached to the surface of the fibre, the medicament at each location being identical.

10. An alginate fibre as claimed in claim 9 wherein the medicament is chlorhexidine acetate.

11. An alginate fibre as claimed in claim 1 wherein the concentration of medicament within the fibre core is 0.01% to 2.0% w/w.

12. A process for the preparation of an alginate fibre as claimed in claim 1, which process comprises the following steps:

(1) spinning a solution of an alginate together with one or more medicaments; and (2) modifying the resulting fibre by attachment of one or more medicaments to the surface thereof, whereby the concentration of medicament attached to the surface of the fibre is 0.01% to 2.0% w/w.

13. A process as claimed in claim 12 wherein step (1) comprises extruding an aqueous solution of sodium alginate and one or more medicaments into a solution containing calcium ions.

14. A process as claimed in claim 12 or claim 13 wherein step (2) comprises immersion of the fibre produced in step (1) in a solution of one or more medicaments.

15. A process as claimed in claim 12 or claim 13 wherein step (2) comprises spraying a solution of one or more medicaments onto the fibre produced in step (1).

16. An alginate fibre obtained by a process as claimed in claim 12.

17. An alginate fabric formed in whole or in part from alginate fibre as claimed in any one of claims 1, 2, 4, 9, 10, 11 or 16.

18. A wound dressing comprising an alginate fabric as claimed in claim 17.

19. A method of treating a wound which method comprises the application to a wound of a wound dressing as claimed in claim 18.

* * * * *